United States Patent [19]

Chang et al.

[11] Patent Number: 5,766,907
[45] Date of Patent: Jun. 16, 1998

[54] METHOD FOR IMMOBILIZATION OF WHOLE MICROBIAL CELLS IN CALCIUM ALGINATE CAPSULES

[75] Inventors: Ho-Nam Chang, Taejon; Gi-Hun Seong, Kimchun; Ik-Keun Yoo, Taejon; Joong-Kon Park, Taegu; Jin-Ho Seo, Soowon, all of Rep. of Korea

[73] Assignee: Korea Advanced Institute of Science & Technology, Taejon, Rep. of Korea

[21] Appl. No.: 501,239

[22] Filed: Jul. 12, 1995

[51] Int. Cl.$^6$ .......................... C12N 11/10; C12N 11/04; C12N 5/00
[52] U.S. Cl. .......................... 435/178; 435/182; 435/382; 435/395
[58] Field of Search .......................... 435/174, 177, 435/178, 182, 382, 395

[56] References Cited

U.S. PATENT DOCUMENTS

| | | | |
|---|---|---|---|
| 4,689,293 | 8/1987 | Gooden | 435/1 |
| 4,695,462 | 9/1987 | Barnes | 424/195.1 |
| 4,722,898 | 2/1988 | Errede | 435/182 |
| 4,749,620 | 6/1988 | Rha et al. | 428/402.2 |
| 4,806,355 | 2/1989 | Gooden | 424/424 |
| 4,828,997 | 5/1989 | Yamaguchi | 435/178 |
| 4,844,896 | 7/1989 | Bohm | 424/89 |
| 4,861,595 | 8/1989 | Barnes | 424/195.1 |
| 5,070,019 | 12/1991 | Hill | 435/178 |
| 5,074,902 | 12/1991 | Connick | 71/79 |
| 5,089,407 | 2/1992 | Baker | 435/179 |
| 5,093,253 | 3/1992 | Nelson | 435/178 |
| 5,175,093 | 12/1992 | Seifert | 435/41 |
| 5,286,495 | 2/1994 | Batich | 424/490 |
| 5,288,632 | 2/1994 | Pannell | 435/243 |

OTHER PUBLICATIONS

Aldercreutz, P. et al., Oxygen Supply to Immobilized Cells: 2. Studies on a Coimmobilized Algae–Bacteria Preparation with in situ Oxygen Generation. Enzyme Microb. Technol., 4:395–400(1982).

de Alterns, E. et al., Effect of Gelatin–Immobilization on the Catalytic Activity of Enzymes and Microbial Cells. Biotechnol. Tech., 2(3):205–210(1988).

Nasri, M. et al., The Use of the Immobilization of Whole Living Cells to Increase Stability of Recombinant Plasmids in *Escherichia coli*. J. Biotechnol., 6:147–157(1987).

Stenroos, S.–L. et al., Production of L–Lactic Acid with Immobilized *Lactobacillus delbrueckii*. Biotechnol. Lett., 4(3):159–164(1982).

Cheetham, P. S. J. et al., Physical Studies on Cell Immobilization Using Calcium Alginate Gels. Biotechnol. Bioeng., 21:2155–2168(1979).

Simionnescu, C. et al., Bioactive Polymers XXX. Immobilization of Invertase on the Diazonium Salt of 4–Aminobenzoylcellulose. Biotechnol. Bioeng., 29:361–365 (1987).

Leo, W. J. et al., Effects of Sterilization Treatments on Some Properties of Alginate Solutions and Gels. Biotechnol. Prog., 6:51–53(1990).

Mansfeld, J. and A. Schellenberger, Invertase Immobilized on Macroporous Polystyrene: Properties and Kinetic Characterization. Biotechnol. Bioeng., 29:72–78(1987).

D'Souza, S. E. and N. Kamath, Cloth Bioreactor Containing Yeast Cells Immobilized on Cotton Cloth Using Polyethylenimine. Appl. Microbiol. Biotechnol., 29:136–140(1988).

Krischke, W. et al., Continuous Production of L–Lactic Acid from Whey Permeate by Immobilized *Lactobacillus casei* Subsp. casei. Appl. Microbiol. Biotechnol., 34:573–578(1991).

Sara, M. and U. B. Sleytr, Use of Regularly Structured Bacterial Cell Envelope Layers as Matrix for the Immobilization of Macromolecules. Appl. Microbiol. Biotechnol., 30:184–189(1989).

Ghosh, S., Immobilization of Baker's Yeast Using Plaster of Paris. Biotechnol. Tech., 2(3):217–219(1988).

Rochefort, W. E. et al., Trivalent Cation Stabilization of Alginate Gel for Cell Immobilization. Biotechnol. Lett., 8(2):115–120(1986).

Birnbaum, S. et al., Covalent Stabilization of Alginate Gel for the Entrapment of Living Whole Cells. Biotechnol. Lett., 3(8):393–400(1981).

Parascandola, P. et al., Immobilization of Yeast Cells by Adhesion on Tuff Granules. Appl. Microbiol. Biotechnol., 26:507–510(1987).

Hasal, P. et al., An Immobilized Whole Yeast Cell Biocatalyst for Enzymatic Sucrose Hydrolysis. Enzyme Microb. Technol., 14:221–229(1992).

Imai, K. et al., Immobilization of Enzyme onto Poly(ethylene–Vinyl Alcohol) Membrane. Biotechnol. Bioeng., 28:198–203(1986).

Nasri, M. et al., Production of Lysine by Using Immobilized Living Corynebacterium sp Cells. Biotechnol. Lett., 11(12):865–870(1989).

Park, T. G. and A. S. Hoffman, Immobilization and Characterization of β–Galactosidase in Thermally Reversible Hydrogel Beads. J. Biomed. Mater. Res., 24:21–38(1990).

Madyastha, K. M. et al., Extracellular Invertase from *Aspergillus athecius*: Isolation and Immobilization. Biotechnol. Lett., 9(8):555–560(1987).

Lim, F. and A. M. Sun, Microencapsulated Islets as Bioartificial Endocrine Pancreas. Science, 210:908–910(1980).

Emr, S. D. et al., An MFαI–SUC2(α–Factor–Tnvertase) Gene Fusion for Study of Protein Localization and Gene Expression in Yeast. Proc. Natl. Acad. Sci., USA, 80:7080–7084(1983).

Cheong, S. H. et al., Microencapsulation of Yeast Cells in the Calcium Alginate Membrane. Biotechnol. Tech., 7(12):879–884(1993).

Primary Examiner—David M. Naff
Attorney, Agent, or Firm—Darby & Darby

[57] ABSTRACT

A method is provided for immobilization of whole microbial cells containing enzymes in Ca-alginate capsules. Whole microbial cells are mixed with a CaCl$_2$ solution, a small amount of xanthan gum is added, the resultant mixture is added drop-wise while stirring to a Na-alginate solution containing a small amount of surfactant which is preferably polyoxyethylenesorbitan monolaurate to obtain the capsules containing the cells. The capsules may be washed with distilled water, hardened by in a CaCl$_2$ solution and incubated in a growth medium. The microbial cells are bacteria or fungi cells and may be recombinant cells.

7 Claims, 5 Drawing Sheets

METHOD FOR IMMOBILIZATION OF WHOLE MICROBIAL CELLS IN CALCIUM ALGINATE CAPSULES

FIELD OF THE INVENTION

The present invention relates to a method for immobilization of whole cell enzyme using calcium-alginate capsule (hereinafter, referred to as "Ca-alginate capsule"), more specifically, to a method for immobilization of highly concentrated whole cell enzyme into perfectly spherical Ca-alginate capsule in a simple and effective manner.

BACKGROUND OF THE INVENTION

A variety of immobilization methods of a highly concentrated culture of microbes have been developed for the purpose of increasing productivity in the fermentation process and enzymatic reaction. In particular, the enzymatic reaction employing immobilized whole cell enzyme has the following advantages: the catalytic power of the enzyme is noticeably stabilized; the enzymes are easily recycled, which naturally cuts down the expense incurred in the process; and, products can be isolated in a simple manner.

One of the most prevailing microbial immobilization methods developed thus far is the cell entrapment method, where microbes are entrapped in gel-cored beads made of either Ca-alginate, polyacrylamide, carrageenan, agarose, gellan gum, or polytetrafluoroethylene(PTFE)(see: U.S. Pat. Nos. 5,175,093; 5,288,632; 5,093,253; 4,722,898; 4,828, 997; 5,070,019; Ghosh, S., Biotechnol. Tech., 2:217–219 (1988)).

The cell entrapment method, however, even though its procedure is simple, has revealed limitations in increasing the concentration of microbes per unit volume of the carrier, because microbes only can grow on the surface or interstitial space of the carrier. Furthermore, said method has been found to have a defect in the immobilization process of microbes from culture, so that free microbes often leak out of the carriers.

On the other hand, the microencapsulation method has been applied in various ways for immobilization of animal, plant, bacterial, algal, or fungal cells(see: U.S. Pat. Nos. 5,286,495; 4,806,355; 4,689,293; Lim, F. et al., Science, 210:908(1980)). However, the said method has also shown a weak-point that a lot of work is essentially required in the process of manufacturing capsules.

Accordingly, there has been a need in the art for the development of a more simple and effective method for immobilization of whole cell enzyme to overcome said problems.

Under the circumstances, the present inventors developed a simple and effective microencapsulation method employing Ca-alginate capsule for immobilization of microbial cells. In contrast to the entrapment method of prior art, the present invention employed liquid-cored spherical capsule that provides more extensive volume for microbial growth, which enables a highly concentrated culture of microbes therein.

SUMMARY OF THE INVENTION

In accordance with the present invention, the inventors prepared Ca-alginate capsule for immobilization of microbes and developed a simple and effective method for immobilization of microbes using the Ca-alginate capsule.

A primary object of the invention is to provide a novel method for immobilization of microbes into Ca-alginate capsule.

BRIEF DESCRIPTIONS OF DRAWINGS

The above and the other objects and features of the present invention will become apparent from following descriptions given in conjunction with the accompanying drawings, in which.

DETAILED DESCRIPTION OF THE INVENTION

In the entrapment method of prior art, microbes are immobilized in a form of Ca-alginate beads which are produced by mixing microbes with sodium alginate(Na-alginate) solution and adding the mixture in a drop-wise into calcium chloride($CaCl_2$) solution. However, the Ca-alginate capsule of the present invention is prepared by employing a series of processes: microbes are first mixed with $CaCl_2$ solution; a small amount of xanthan gum is added; then the mixture is added drop-wise while stirring to Na-alginate solution containing a small amount of surfactant, to produce Ca-alginate capsule. The capsules thus formed are washed, condensed, and incubated in a growth medium. The Ca-alginate capsule of the invention should be perfectly spherical, because formation of a tail on a capsule, which easily breaks off, causes microbes to escape through the surface of the capsule and grow in the medium, which finally interferes with cultivation of a highly concentrated microbes and thus decreases the productivity.

To obtain the perfectly spherical capsule of the invention, xanthan gum is added to $CaCl_2$ solution and the geometrical feature of the Na-alginate solution being stirred is controlled in a proper manner, because both the capsule membrane formation rate and the shear stress between the liquid drops of $CaCl_2$ solution and the Na-alginate solution being stirred determine the shape of capsule.

Furthermore, to prevent swelling and rupturing of the capsules which might occur by the accumulation of $CO_2$ produced during incubation, a small amount of surfactant which increases gas permeability of the membrane is used, and $CaCl_2$ is added to the growth medium to stabilize the capsule membrane which is formed by ionic bond between calcium and alginate, to prevent swelling of the membrane and to maintain high concentration of microbes within a capsule.

The Ca-alginate capsule produced by the method of the invention shows a wide range of applicability: for example, the capsules can be used in common fermenters or reactors for a variety of whole cell enzymatic reactions such as ethanol or lactic acid fermentation; and, they can be also used as a whole cell enzyme for specific enzymatic reactions requiring certain enzyme activities of the microbes, which greatly simplifies the enzyme immobilization processes.

The present invention is further illustrated in the following examples, which should not be taken to limit the scope of the invention.

Example 1: Immobilization of whole cell enzyme using Ca-alginate capsule

A recombinant yeast, Saccharomyces cerevisiae SEY2102 (MATα ura3-52, leu2-3, -122 his 4-519) containing 2μ based plasmid pBR58 encoding sucrose invertase, an enzyme that hydrolyses sucrose into glucose and fructose (see: Emr, S. D. et al., Proc. Natl. Acad. Sci. USA, 80:7080 (1983)), was employed as a microbe.

Figure 1:
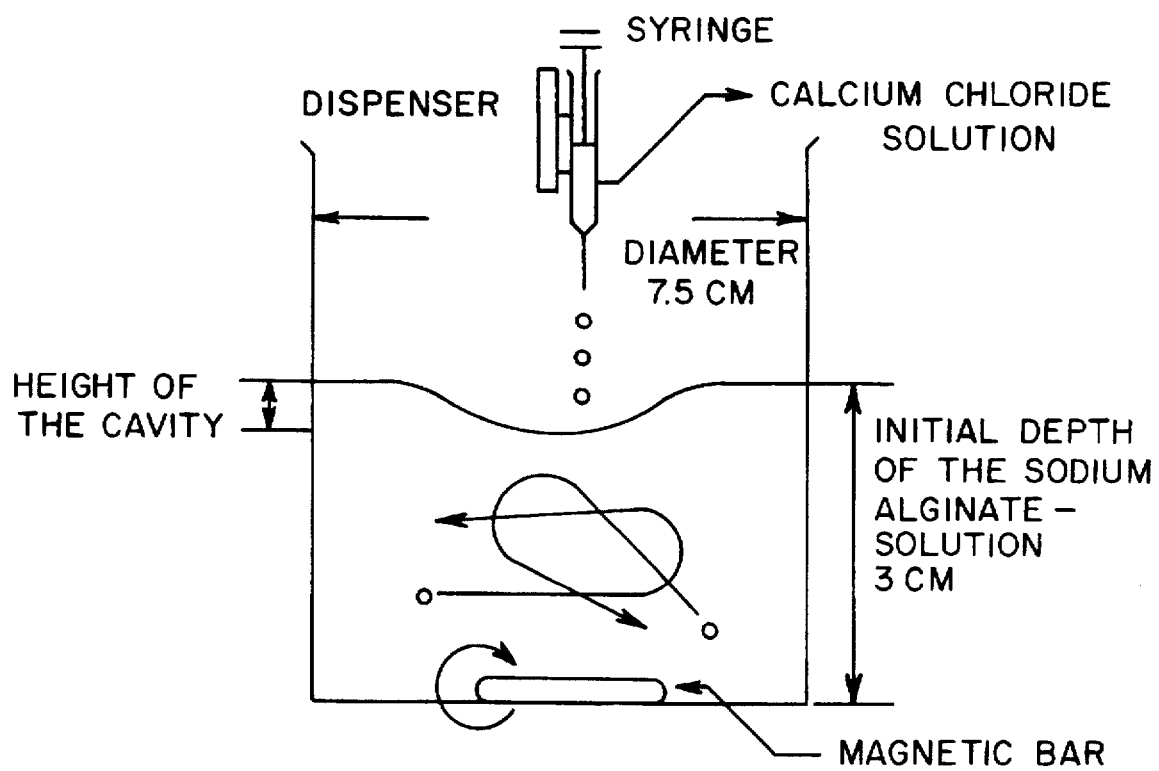
FIG. 1 is a schematic diagram depicting the microencapsulation method in which Ca-alginate capsule is produced.

Saccharomyces cerevisiae SEY2102 was cultured in a growth medium(containing 20 g/L glucose, 6.67 g/L Bacto yeast nitrogen base(YNB) free of amino acid, and 5 g/L casamino acid). 15 ml of the cell broth was centrifuged, and the precipitate was mixed well with 100 ml of a mixture of 1.3% (w/v) $CaCl_2$ and 0.26% (w/v) xanthan gum under room temperature. By the aid of syringe of a 22 G needle, the mixture was added to 0.6% (w/v) Na-alginate solution containing 0.1% (v/v) Tween 20 while stirring and left to react for 10 minutes, to produce perfectly spherical capsules of 0.01 $cm^3$. As shown in FIG. 1, the reactor employed in the Examples was a cylindrical type of vessel of 7.5 cm in diameter, where the depth of Na-alginate solution was 3 cm and the height of a whirlpool cavity that occurs while stirring was 1 cm. As a surfactant, Tween 20 was added to the solution to permit $CO_2$ produced by yeast cells to easily diffuse out through the capsule membrane. The capsule produced was washed with distilled water for 10 minutes, added to 1.3% (w/v) $CaCl_2$ solution, and stirred for 20 minutes for hardening. Then, the capsules were put in a growth medium and incubated in a shaking incubator at 30° C. At this time, 0.5 %(w/v) $CaCl_2$ solution was added to prevent swelling of the capsules.

Comparative Example 1: Immobilization of whole cell enzyme using Ca-alginate bead In a way of comparison with the microencapsulation method of Example 1, the Ca-alginate beads were prepared by the entrapment method employing the same yeast cell as in the Example 1: Yeast cells were harvested from 5 ml of cell broth and uniformly mixed with 0.6% (w/v) Na-alginate solution. The mixture was dripped into 1.0% (w/v) $CaCl_2$ solution by the aid of syringe of a 22 G needle to produce the beads. Then, the beads thus produced were washed with distilled water and hardened in 1.0% (w/v) $CaCl_2$ solution for 20 minutes, and incubated in a growth medium in the same manner as Example 1.

Figure 2:
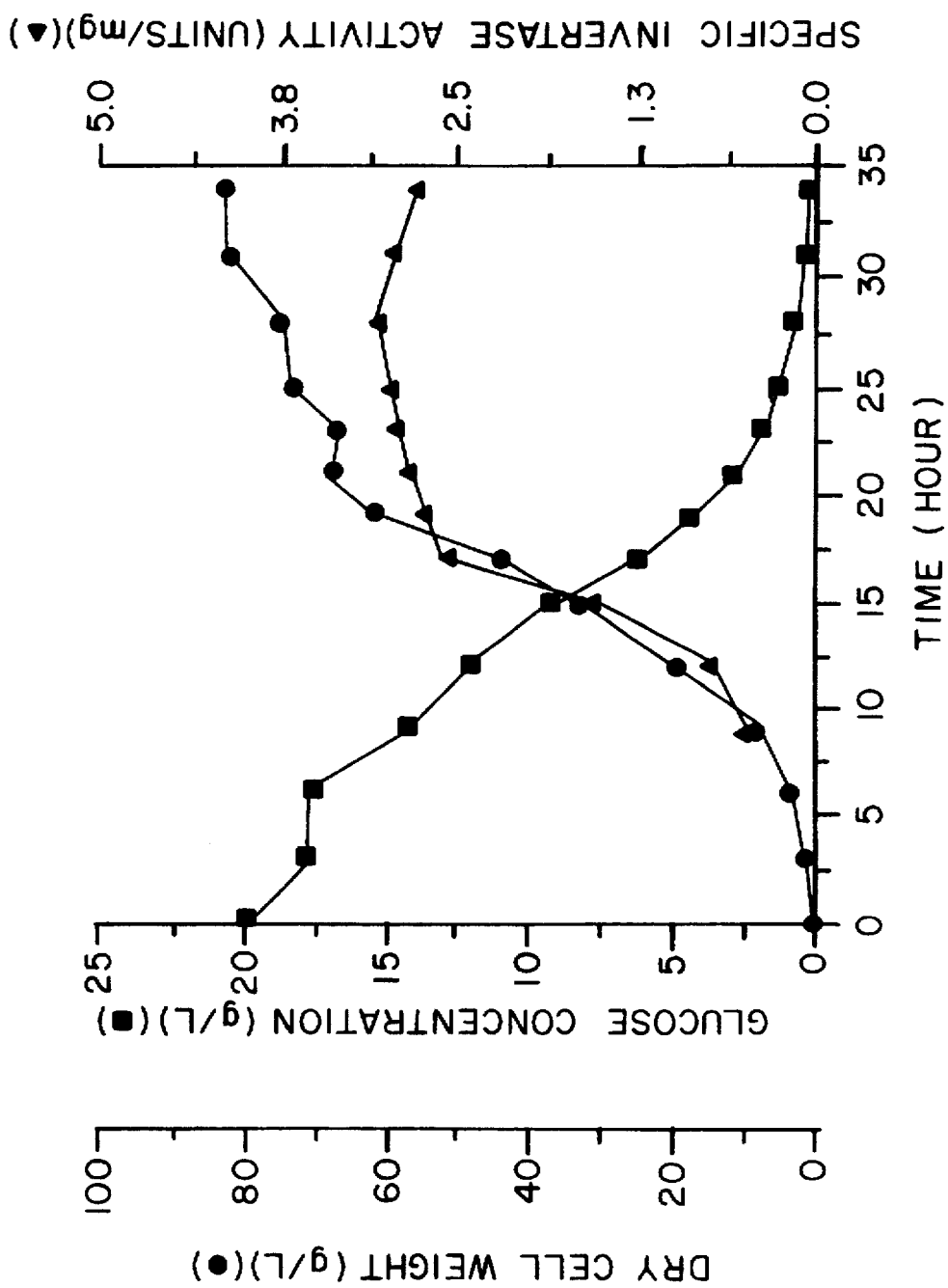
FIG. 2 is a graph showing the specific invertase activity of recombinant yeast cells immobilized in the Ca-alginate capsule.
Figure 3:
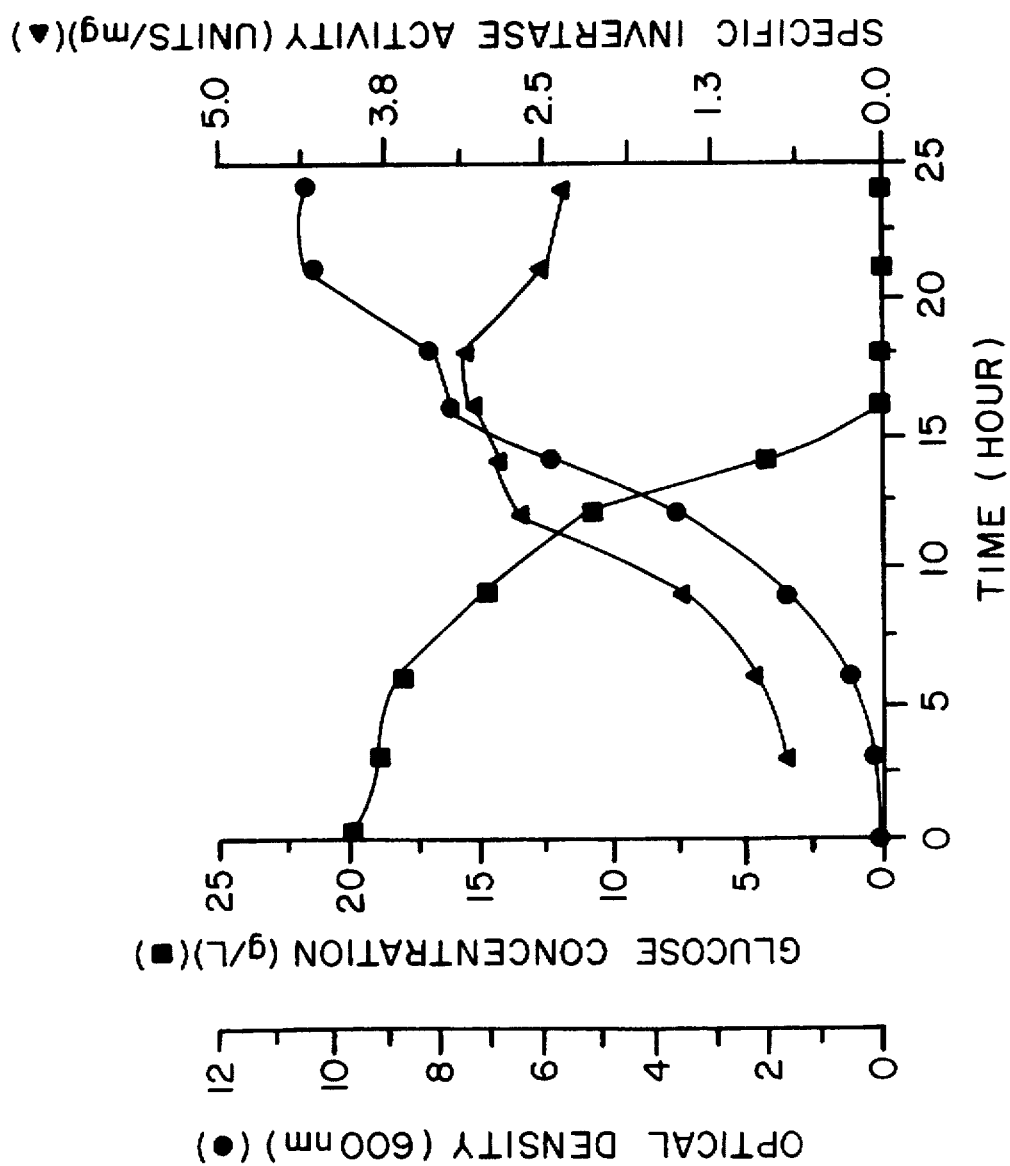
FIG. 3 is a graph showing the specific invertase activity of free recombinant yeast cells.

Example 2: The specific invertase activity of whole cell enzyme immobilized in the Ca-alginate capsule The specific invertase activity(SIA) of the yeast cell immobilized in the Ca-alginate capsule and the free yeast cell was shown in FIGS. 2 and 3, respectively. In this example, five hundred immobilized capsules were incubated in 100 ml of the growth medium; and, one unit(1 U) of the invertase activity was defined as the amount of whole cells that forms 1 μmol of glucose at 30° C. and pH 4.9 for one minute. As can be seen in FIGS. 2 and 3, it was found that the maximum value of the specific invertase activity of the immobilized cell was about 2.98 units/mg, which was almost same as that obtained from a free cell culture(3.01 units/mg), indicating that the enzyme activity of the yeast cell was not affected by the immobilization process. On the contrary, the concentration of yeast cells cultured within the capsule was over 83 g/L, which was 20 times as high as that of a free cell culture(4.01 g/L). As clearly illustrated in the above results, considering that the total invertase activity is a product of the concentration of yeast cells and the specific invertase activity, the cells immobilized in the Ca-alginate capsules had much higher total invertase activity than free cells.

Figure 4:
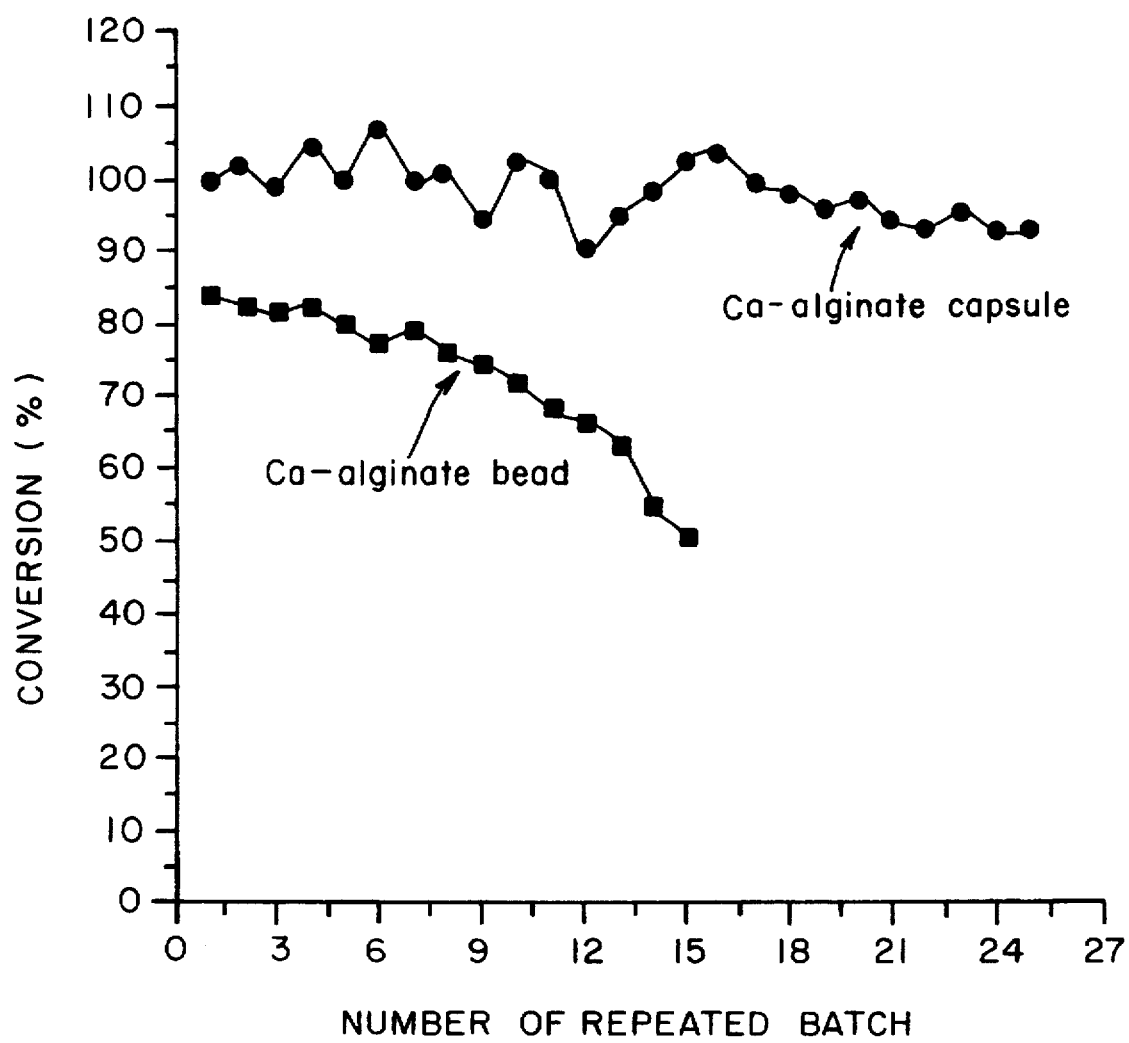
FIG. 4 is a graph showing a comparison of enzymatic sucrose hydrolysis employing the Ca-alginate capsule and the Ca-alginate bead; and, FIG. 5 is a graph showing a continuous reaction of enzymatic sucrose hydrolysis by the recombinant yeast cells immobilized in the Ca-alginate capsule.

Example 3: Sucrose hydrolysis activity of whole cell enzymes immobilized in the Ca-alginate capsule Sucrose hydrolysis activity of whole cell enzyme immobilized in the Ca-alginate capsule(-o-) was compared with the Ca-alginate bead(-□-) (see: FIG. 4). The beads and capsules, two thousand each, were added to 100 ml of 0.5 M sucrose solution and allowed to repeat two-hour batch reaction. The reaction temperature was controlled at 45° C., but pH was not controlled. As can be seen in FIG. 4, the capsules maintained over 90% of conversion after twenty-five batch reactions, while the beads represented only below 50% of conversion over fifteen batch reactions due to a continuous leak-out of yeast cells. From these results, it could be concluded that the microencapsulation method of the present invention provides a more improved productivity and is more effective in isolating cells, compared to the entrapment method of prior art.

Figure 5:
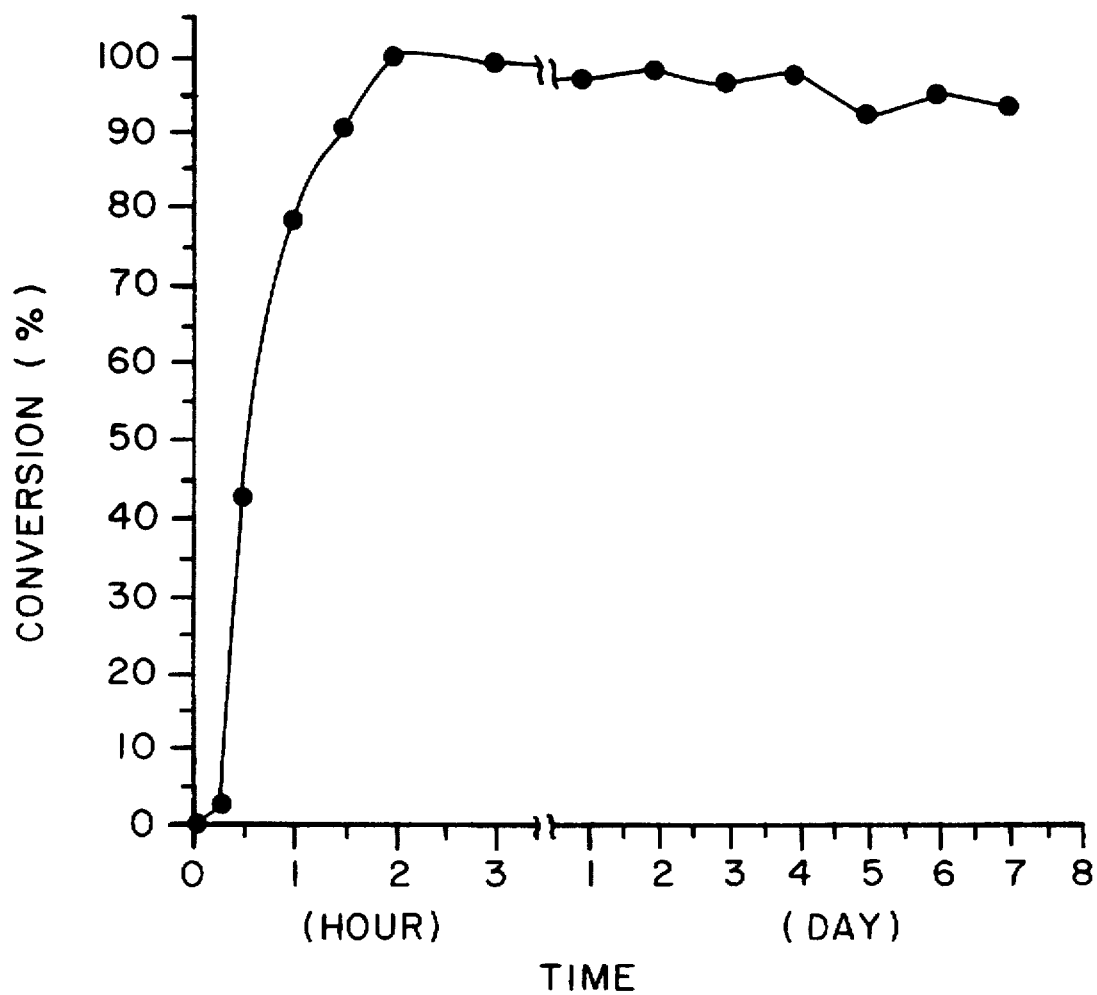

Example 4: Continuous enzymatic sucrose hydrolysis of whole cell enzyme immobilized in the Ca-alginate capsule Ca-alginate capsule prepared in Example 1 was employed in a continuous reaction of enzymatic sucrose hydrolysis (see: FIG. 5). A common, cylindrical packed bed column which has 60 ml of working volume was filled up with the capsules and then 0.3 M sucrose solution was infused into the column at a flow rate of 60 ml/hr(dilution rate: 1.08 $hr^{-1}$). The reaction temperature was controlled at 45° C., but pH was not controlled. The reaction reached a steady state in two hours since the continuous reaction was initiated, and almost over 95% of conversion could be maintained over 7-day work.

As clearly shown and explained above, the present invention provides a method for immobilization of highly concentrated whole cell enzyme using Ca-alginate capsule in a simple and effective manner. The whole cell enzyme immobilized in the Ca-alginate capsule of the present invention provides a more improved productivity; and, therefore, it can be applied in a variety of enzymatic reactions requiring enzyme activities of the cells such as bacteria, yeast, fungi, and their recombinant cells.

What is claimed is:

1. A method for immobilization of whole microbial cells containing enzymes in perfectly spherical Ca-alginate capsules, which comprises the steps of: mixing whole microbial cells with a $CaCl_2$ solution to form a microbial cell/$CaCl_2$ solution; adding xanthan gum to said microbial cell/$CaCl_2$ solution to form a xanthan gum/microbial cell/$CaCl_2$ solution; and adding the xanthan gum/microbial cell/$CaCl_2$ solution dropwise to a Na-alginate solution containing polyoxyethylenesorbitan monolaurate while stirring to obtain said Ca-alginate capsules contianing whole microbial cells.

2. The method of claim 1, wherein said whole cells containing enzymes are selected from the group consisting of bacteria and fungi.

3. The method of claim 2, wherein the bacteria are recombinant bacteria.

4. The method of claim 2, wherein the fungi is yeast.

5. The method of claim 2, wherein the fungi are recombinant fungi.

6. The method of claim 4, wherein the yeast are recombinant yeast.

7. The method of claim 1, which further comprises the steps of washing the Ca-alginate capsules with distilled water; hardening the Ca-alginate capsules by adding the washed Ca-alginate capsules to $CaCl_2$ solution; and incubating the hardened Ca-alginate capsules in a growth medium.

* * * * *